United States Patent

Spurling et al.

[11] Patent Number: 4,513,537
[45] Date of Patent: Apr. 30, 1985

[54] DEVICE FOR PREPARING THIN SPECIMENS

[75] Inventors: Robert A. Spurling, Thousand Oaks; Burton I. Davis, Camarillo; Norman G. Taylor, Thousand Oaks, all of Calif.

[73] Assignee: Rockwell International Corporation, El Segundo, Calif.

[21] Appl. No.: 526,734

[22] Filed: Aug. 26, 1983

[51] Int. Cl.³ .............................................. B24B 11/00
[52] U.S. Cl. .......................................... 51/71; 51/57; 51/90; 51/119; 51/216 LP
[58] Field of Search .................. 51/27, 57, 58, 71, 90, 51/96, 105 LG, 124 R, 124 L, 216 LP, 229, 274, 119, 120

[56] References Cited

U.S. PATENT DOCUMENTS

| | | | |
|---|---|---|---|
| 998,101 | 7/1911 | Laabs | 51/105 LG |
| 1,146,513 | 7/1915 | Perkins | 51/57 |
| 2,371,303 | 3/1945 | Liebowitz | 51/57 X |
| 3,167,886 | 2/1965 | Harrison | 51/90 X |
| 3,732,647 | 5/1973 | Stith | 51/90 X |
| 3,782,045 | 1/1974 | Kanada | 51/124 L |

Primary Examiner—Robert P. Olszewski
Attorney, Agent, or Firm—H. Frederick Hamann; Craig O. Malin

[57] ABSTRACT

A mechanical grinding device is provided for preparing very thin specimens such as transmission electron microscopy specimens. The specimens are held on the end of a long rod which is pressed against a spherical tool by the weight of the rod. The opposite end of the rod extends through a hole in a pivot plate which is spaced above the tool. The tool is mounted on a tool holder which is eccentrically positioned on a rotating base by a pivot. As the base rotates, the tool holder moves and a concave surface is ground in the specimen, thus thinning it.

3 Claims, 12 Drawing Figures

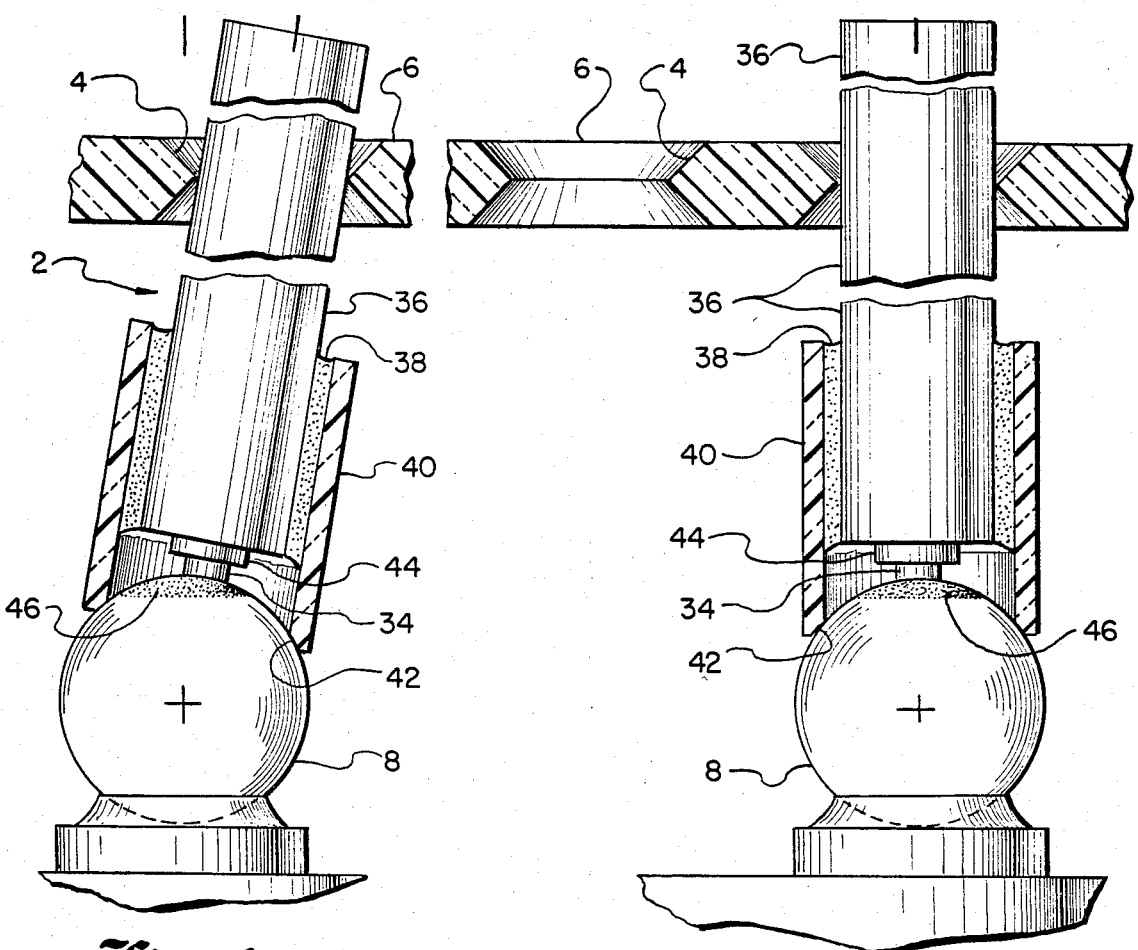
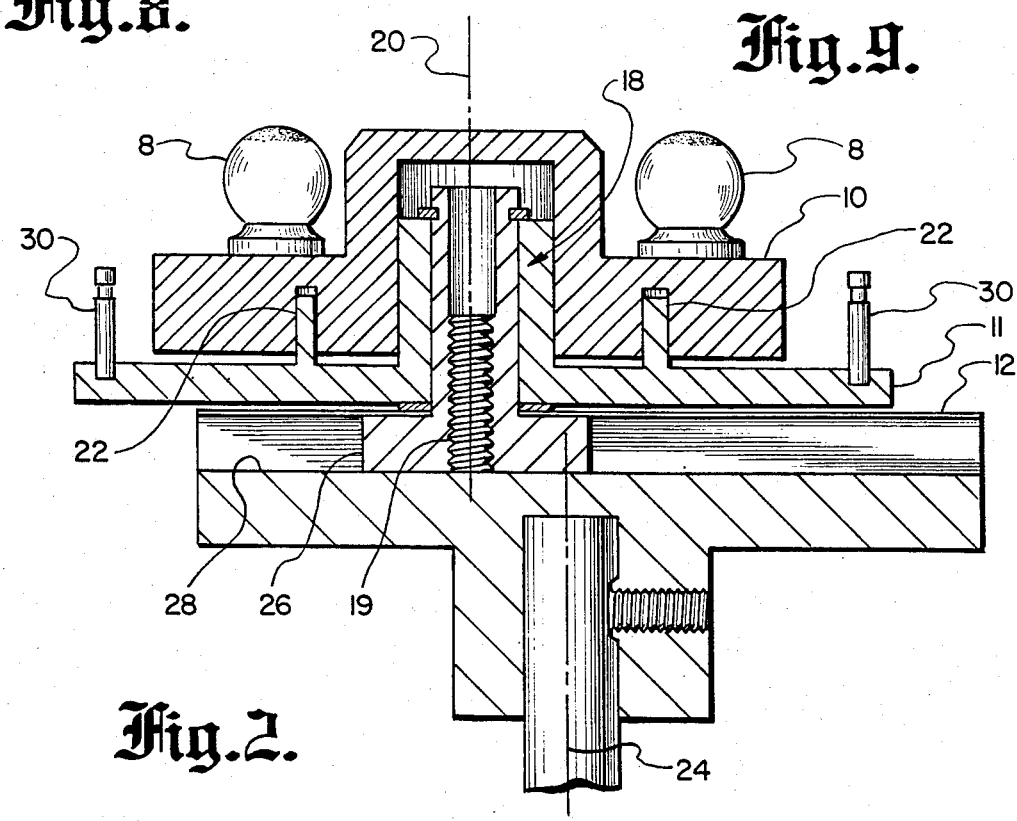

Fig. 3.
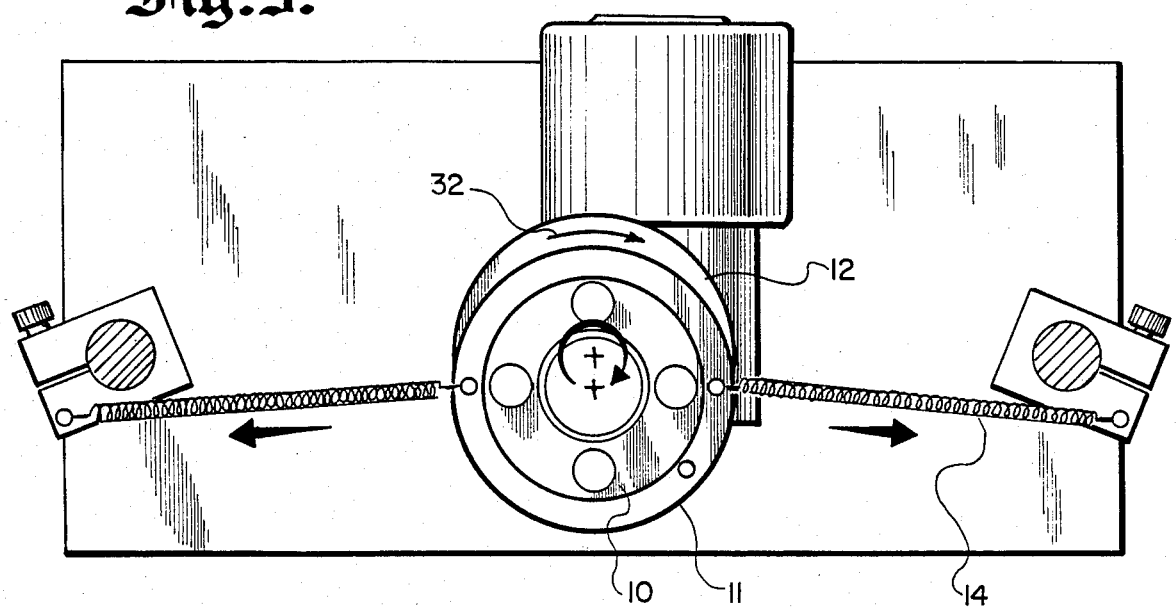
Fig. 4.a.
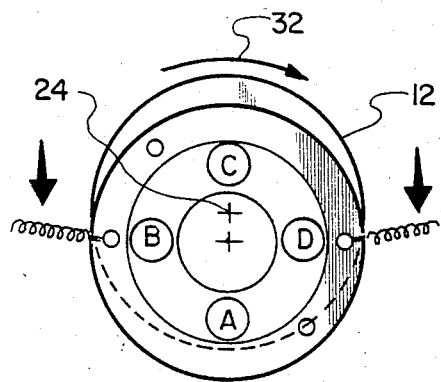
Fig. 4.c.
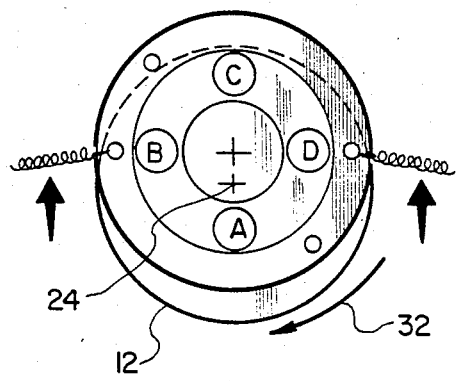
Fig. 4.b.
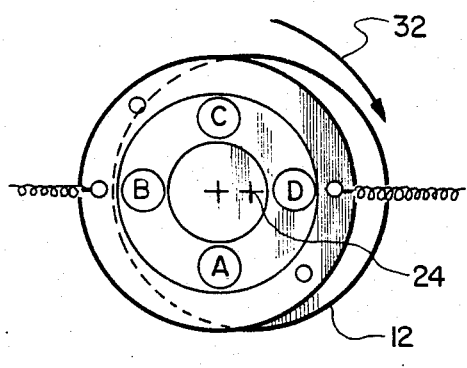
Fig. 4.d.
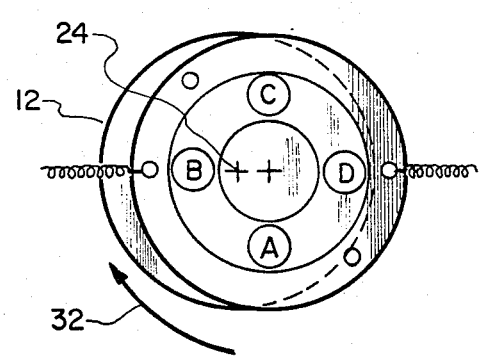

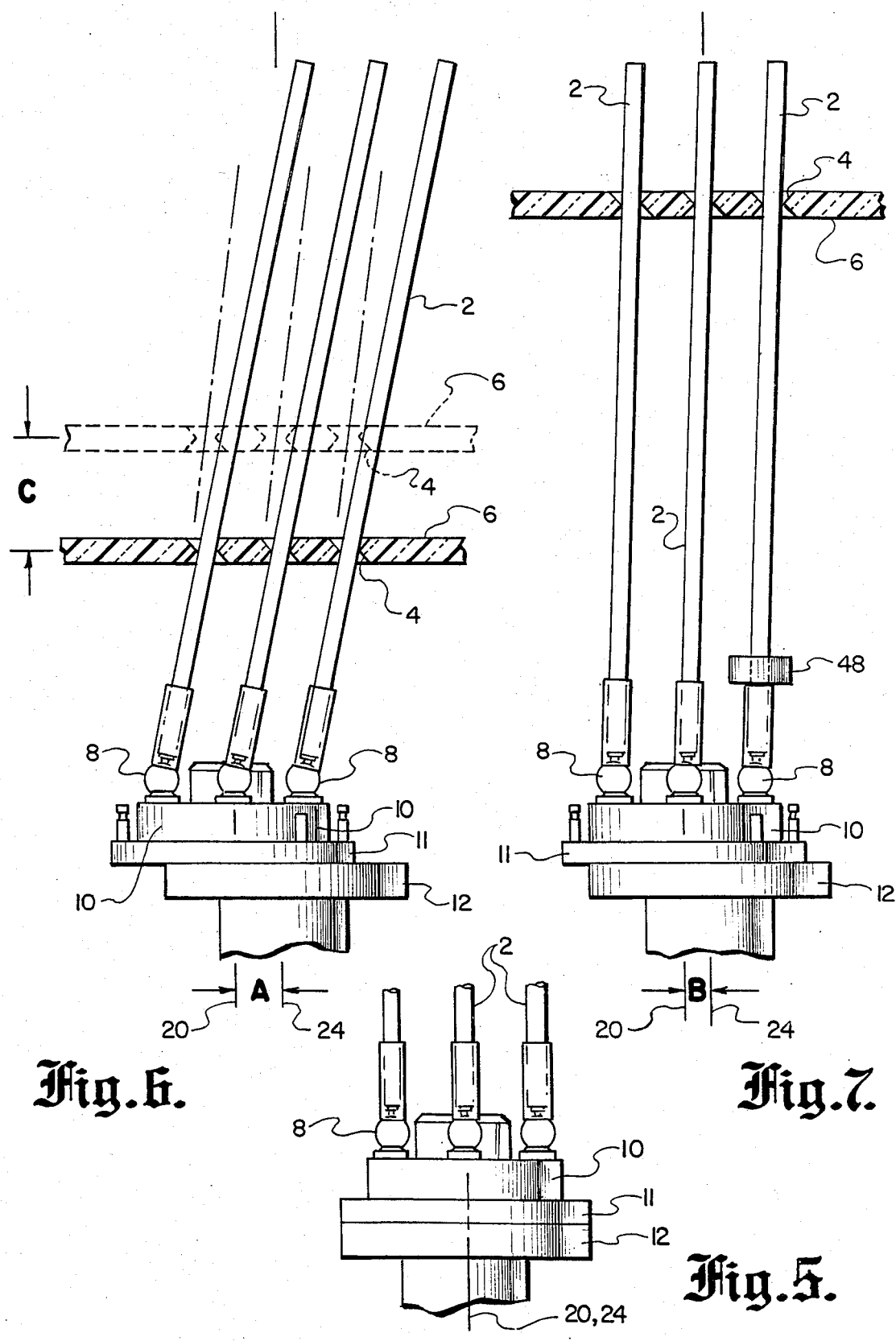

DEVICE FOR PREPARING THIN SPECIMENS

BACKGROUND OF THE INVENTION

This invention relates to the field of specimen preparation, and particularly to the preparation of thin specimens for use in transmission electron microscopy.

Sample preparation is an important and time consuming requirement in the microscopy of materials. The samples required for transmission electron microscopy must be very thin, on the order of 1000 angstroms. Such specimens are extremely fragile and difficult to handle, both during the sample preparation and during the subsequent microscopy.

The principle method for producing thin specimens of non-conductive materials for examination by transmission electron microscopy is by ion beam milling. The major disadvantage of the ion thinning technique is that it is slow. For dense, fine-grained ceramics or for materials composed of elements of high atomic number, a thinning rate of about 1 um/hr is obtained. Higher rates can be achieved with special purpose, high intensity or high voltage ion beams, but usually to the detriment of specimen quality because of radiation damage or sample heating. Therefore, emphasis is placed on first producing as thin a section as possible by mechanical means in order to minimize ion milling time. For most materials, sections thinner than 75-125 um are extremely fragile and difficult to prepare mechanically. Such sections may still require several days to thin by ion miling even after extensive mechanical thinning.

SUMMARY OF THE INVENTION

It is an object of the invention to provide a grinder which can automatically reduce the center thickness of specimens for transmission electron microscopy (TEM) prior to ion beam milling.

It is an object of the invention to provide a device which can grind TEM specimens down to a thickness which reduces the amount of ion beam milling required to produce a completed specimen.

It is an object of the invention to provide a device which can produce TEM specimens which are dished, and which are less suceptible to breakage during handling than flat specimens.

According to the invention, a concavity is ground into a starting blank using a tool with a spherical grinding surface. The thick rim section of the concavity gives the specimen both strength and rigidity for handling and the thin center section of the concavity presents a minimum of material to be ion milled.

To grind the concavity, a starting blank is cemented onto the end of a long rod which is pressed against the spherical grinding surface by the weight of the rod. The opposite end of the rod extends through a hole in a pivot plate which is spaced above the grinding surface. The grinding surface is provided by a metal ball which is eccentrically mounted on a rotatable base. A small cylinder, or ferrule, extending from the working end of the rod rides on a portion of the ball. The ferrule prevents the rod from sliding off the ball and helps control the grinding rate. An abrasive material is placed on the ball so that, when the base is rotated, the ball grinds a matching concavity on one side of the starting blank.

The rate of grinding is controlled by the weight of the rod and by the surface area of the ferrule which is ground along with the specimen. A spherical seat matching the ball is formed on the inside rim of the ferrule. As grinding continues, the width of the spherical seat increases as both the ferrule and specimen are ground. Consequently, the grinding pressure shared by the specimen is correspondingly reduced.

These and other objects and features of the invention will be apparent from the following detailed description taken with reference to the accompanying drawings.

BRIEF DESCRIPTION OF THE DRAWINGS

FIG. 2 is a cross-sectional side view showing the adjustable eccentric coupling between the rotatable base and the tool holder;

FIG. 3 is a top view of the invention without the specimen holders and pivot plate;

FIG. 4 is a top view of the rotatable base, eccentric pivot, and tool holder in four different positions (A, B, C, and D).

FIG. 5 is a side view showing the relationship of the specimen holders and the tool when the center line of the rotatable table and the eccentric pivot coincide;

FIG. 6 shows the same relationship as FIG. 5 except the centerlines are displaced a distance "a", and two positions are shown for the pivot plate;

FIG. 7 shows the same relationship as FIG. 5 except the centerlines are displaced by a distance "b";

FIG. 8 is a detail showing the specimen bearing against the spherical tool when the specimen holder and tool are oriented as shown in FIG. 6; and FIG. 9 is a detail showing the specimen bearing against the spherical tool when the orientation is as shown in FIG. 5.

DESCRIPTION OF THE PREFERRED EMBODIMENT

Figure 1:
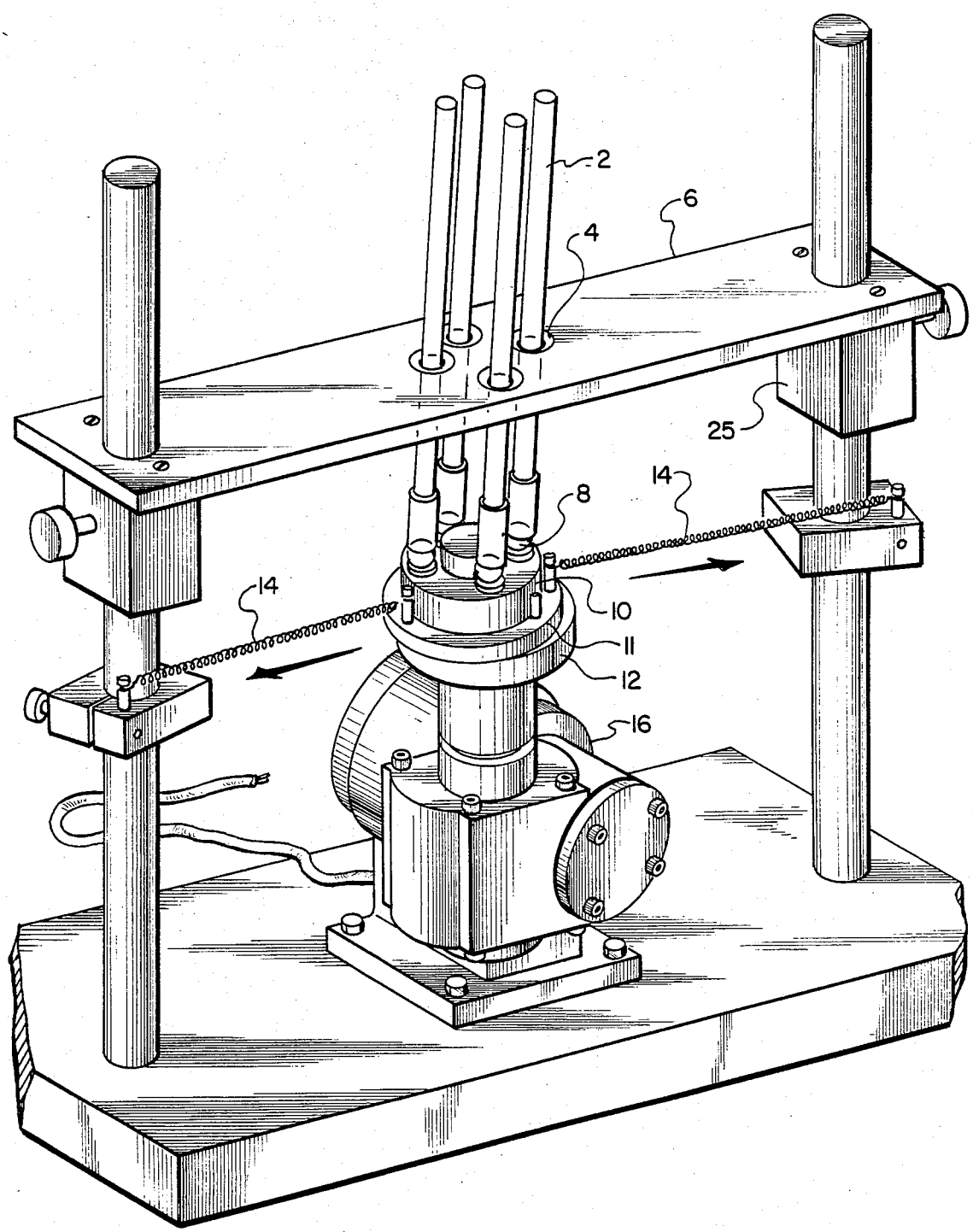
FIG. 1 is a perspective view of the invention being used to prepare four specimens.

FIG. 1 shows the invention in operation to grind four specimens for transmission electron microscopy. Each specimen is mounted on the end of a specimen holder 2. Specimen holder 2 extends through a hole 4 in pivot plate 6. The specimen is bonded onto the end of specimen holder 2 and it bears on the spherical surface of tool 8. Tool 8 is rigidly mounted on tool holder 10 which in turn is coupled to rotatable base 12 by eccentric pivot 11. Eccentric pivot 11 is eccentrically positioned on base 12 so that when base 12 rotates, tool 8 moves along a circular path. Springs 14 keep eccentric pivot 11 and tool holder 10 in orientation on rotatable base 12 while still allowing them to move in a circular path as a result of their eccentric coupling to rotatable base 12. Base 12 is rotated by motor 16.

The eccentric, pivotable coupling between rotatable base 12 and eccentric pivot 11 is shown in FIG. 2. Eccentric pivot 11 is coupled to base 12 by bearing 18 and set screw 19 so that it can rotate about pivot centerline 20. Tool holder 10 slips onto eccentric pivot 11 and is held there by pins 22. The eccentricity of pivot 11 with respect to centerline 24 of base 12 is adjustable by sliding retaining piece 26 along dovetail groove 28. As base 12 rotates about its centerline 24, eccentric pivot 11 with tool holder 10 is free to rotate about pivot centerline 20. However, springs 14 attached to pins 30 maintain the radial orientation of the tool holder while permitting it to be cranked around a circular orbit by bearing 18.

FIG. 3 is a top view of the grinder without pivot plate 6 and specimen holders 2. Arrow 32 shows the rotation of rotatable base 12 while tool holder 10 and eccentric pivot 11 are held in the same radial orientation by springs 14.

FIGS. 4A–4D show how the spherical tools 8 (separately identified as A, B, C, and D) maintain their radial orientation as base 12 rotates through four quadrants about its centerline 24.

FIGS. 5, 6, and 7 show how changing the eccentricity changes the grinding motion. If eccentric pivot 11 is adjusted so that its centerline 20 is coincidental with the centerline 24 of rotatable base 12 as shown in FIG. 5, tool holder 10 and eccentric pivot 11 do not move when base 12 rotates. However, if eccentric pivot 11 is moved so that its centerline 20 is spaced a distance "a" from centerline 24 of base 12 (FIG. 6), then tool holder 10 will follow a circular orbit having a diameter equal to "2a". If the amount of eccentricity is reduced to a distance "b" as shown in FIG. 7, the orbit followed by tool holder 10 is reduced to a diameter of "2b" distance.

FIGS. 6 and 7 also show how changing the height of pivot plate 6 changes the position of specimen holder 2 with respect to tool 8. The specimen holder pivots against the sides of hole 4 in plate 6 as tool 8 moves through its circular orbit. When plate 6 is raised (using adjustable support 25, FIG. 1) a distance "c" as shown by the dashed lines in FIG. 6, the specimen holders are maintained in a more vertical position by pivot plate 6.

FIGS. 8 and 9 show how specimen 34 is held against spherical tool 8 (for example a ½ inch diameter ball bearing) during grinding. Specimen holder 2 comprises a rod 36 (for example a 9 mm diameter pyrex rod) which is cemented with thermoplastic cement 38 inside a ferrule 40 (for example a 11 mm OD pyrex tubing). The fit should be an easy slip fit enabling ferrule 40 to move easily on rod 36 when cement 38 is softened. Preparation of a new specimen holder 2 involves softening cement 38 and grinding the ends of ferrule 40 and rode 36 square against a glass plate. This is followed by retracting rod 36 so that when placed on spherical tool 8 as shown in FIGS. 8 and 9, only ferrule 40 contacts spherical tool 8. A spherical seat 42 which is 0.25 to 0.5 mm wide on the inner edge of the ferrule can then be ground.

Following preparation of specimen holder 2, specimen 34 (which is typically a 3.00 mm diameter by 100 micrometer thick disk mounted on a carrier 44) is cemented to the center of rod 36. Accurate alignment of the center of specimen 34 with the center of rod 36 can be accomplished by warming ferrule 40 to soften cement 38 and the sliding rod 36 to seat specimen 34 against tool 8 as shown in FIG. 9. The point of contact between specimen 34 and tool 8 may be revealed by marking tool 8 with a grease pencil and rubbing specimen holder 2 against tool 8. A grease spot will then be transferred to the specimen surface where contact occurs. If the contact is not in the center of specimen 34, the cement holding carrier disk 34 to the end of rod 36 can be softened with a heat gun and the carrier disk and rod repositioned to bring the center of specimen 34 to the position of contact with tool 8. This repositioning is repeated until the point of contact coincides with the center of specimen 34.

Grinding can then proceed by charging tool 8 with an abrasive (for example 1 micron diamond paste and a drop of kerosene), placing specimen holder 2 on tool 8 as shown in FIG. 1, and turning on motor 16. The rate of grinding specimen 34 is controlled by the weight of specimen holder 2 and by the rate of grinding the ferrule's spherical seat 42. As seat 42 widens, the rate of grinding specimen 34 decreases. When the width of seat 42 reaches about 1 mm, the ferrule should be ground again on a flat plate to bring it back to the original 0.25 to 0.5 mm. The grinding rate can also be increased by adding weights such as cylinders 48 shown in FIG. 7.

The depth, $\delta$, of the convavity ground in specimen 34 may be monitored by measuring the diameter of the concavity, D, and using the small angle approximation $$\delta = D^2/8R$$

where R is the radius of the sphere. The measurement of the concavity diameter can be done easily using a low power microscope with a filar micrometer ocular.

The dimensions of the sphere and the rod diameter given in the example above were chosen to optimize the depth of the concavity while allowing a reasonable limiting angle (the angle of shadowing cast by the unground rim). Small angles (less than 10 degrees) of thinning require either the use of thinner specimens or larger fixture sizes. The thin center section created by the concavity presents a minimum of material to be ion milled, whereas the thicker rim section gives strength and rigidity for handling fragile specimens during ion milling and subsequent handling under the transmission microscope.

Numerous variations and modifications can be made without departing from the invention. For example, ferrule 40 could be coupled to rod 36 by threads rather than by using thermoplastic cement 38. Accordingly, it should be understood that the form of the invention described above is illustrative and is not intended to limit the scope of the invention.

What is claimed is:

1. A device for dishing specimens comprising:
   a rotatable base;
   a tool holder eccentrically positioned on said rotatable base by a pivot;
   a tool mounted on said tool holder, said tool having a spherical surface;
   a pivot plate having a hole extending therethrough, said plate being positioned above and spaced from said rotatable base;
   a support for holding said pivot plate, and a spring coupled to said support and to said eccentric pivot to hold said tool in the same radial orientation as said base rotates;
   a specimen holder positionable on said tool, said specimen holder comprising:
      a rod extendable through said hole in said pivot plate;
      means for mounting a specimen on an end of said rod;
      a ferrule extending out from said end of said rod, said ferrule being positionable on said spherical surface with the specimen bearing on said spherical surface between said end of said rod and said spherical surface;
      whereby rotation of said base causes said tool to grind against said specimen and form a dish in the surface of said specimen.

2. The device as claimed in claim 1, including a plurality of said tools, said specimen holders, and said holes in said pivot plate, whereby a plurality of samples can be dished at the same time.

3. The device as claimed in claim 1 wherein said support is adjustable.

* * * * *